United States Patent
Wadsworth et al.

(10) Patent No.: US 6,945,261 B2
(45) Date of Patent: Sep. 20, 2005

(54) APPARATUSES, SYSTEMS AND PROCESSES FOR SURFACE CLEANING

(75) Inventors: John Wadsworth, Bountiful, UT (US); Stefan Münch, Chicago, IL (US)

(73) Assignee: Nalco Company, Naperville, IL (US)

(*) Notice: Subject to any disclaimer, the term of this patent is extended or adjusted under 35 U.S.C. 154(b) by 0 days.

(21) Appl. No.: 10/658,719

(22) Filed: Sep. 9, 2003

(65) Prior Publication Data

US 2005/0051197 A1 Mar. 10, 2005

(51) Int. Cl.[7] ................................................. B08B 3/02
(52) U.S. Cl. ........................ 134/95.3; 134/174; 134/198
(58) Field of Search ......................... 134/98, 95.3, 174, 134/198; 239/101

(56) References Cited

U.S. PATENT DOCUMENTS

| | | | | |
|---|---|---|---|---|
| 3,675,851 A | * | 7/1972 | Merfeld et al. ............. | 239/318 |
| 4,897,122 A | * | 1/1990 | Schreiber et al. ............. | 134/29 |
| 4,897,350 A | * | 1/1990 | El-Megeed et al. ......... | 435/115 |
| 6,206,980 B1 | * | 3/2001 | Robinson ..................... | 134/21 |
| 6,258,177 B1 | * | 7/2001 | Eastman et al. ............... | 134/6 |
| 6,571,805 B2 | * | 6/2003 | Hoenisch et al. ........ | 134/22.12 |
| 2002/0033185 A1 | * | 3/2002 | Hoenisch et al. ........ | 134/22.12 |

* cited by examiner

Primary Examiner—Michael Barr
Assistant Examiner—Saeed Chaudhry
(74) Attorney, Agent, or Firm—Michael B. Martin; Thomas M. Breininger (57) ABSTRACT

Described and claimed are apparatuses and systems for surface cleaning comprising a pump and an applicator connected to the pump through which one or more cleaning agents can be applied to the surface at an operating pressure that is about 600 PSI or less and an operating flow rate that is about 1 gal/min or less.

14 Claims, 5 Drawing Sheets

APPARATUSES, SYSTEMS AND PROCESSES FOR SURFACE CLEANING

FIELD OF THE INVENTION

The present invention relates generally to apparatuses, systems and methods for cleaning. More specifically, the present invention relates to apparatuses, systems and methods for cleaning surface, such as surfaces associated with air handler systems, particularly, the coils and fins associated with these systems wherein dust, smoke, lint, dirt and other airborne constituents can be deposited on the surface thereof during use of same, for example, thus rendering these surfaces in need of cleaning.

BACKGROUND OF THE INVENTION

In general, the atmosphere can act as a carrier for a number of different types of pollutants, contaminants and/or other airborne constituents, such as dust, lint, pollen, moisture, smoke, odors, fungus, mold and/or the like. As they move through the atmosphere, the airborne constituents can be deposited on a number of different surfaces associated with a variety of different products (i.e., windows, cars, etc.). The products are then cleaned (i.e., window cleaning, car washing, etc.) at some point in time due to same.

Airborne constituents, particularly airborne pathogens, are receiving significant attention from Government, Industry, Healthcare institutions and the media with respect to indoor air-quality issues. In general, typical air handler systems, such as HVAC systems, use coils and fins as a medium to provide heating and cooling exchange. Air is pulled across the surface of the coils and fins to make the heating or cooling transfer. However, airborne constituents, such as dust, lint, smoke, odors, fungus, mold and/or other like matter can be deposited on the surface of such air handler systems during use. The deposited matter can decrease the efficiency of the air system, thus increasing energy costs.

Further, the decrease in efficiency of the air system can have an adverse effect on the air quality. In this regard, there exists a greater potential for spreading odors, mold, fungus spore and/or the like throughout the room or building and for creating a breeding ground for a myriad of pathogens, such as *Legionella*. Thus, indoor air quality is diminished if the air system is not cleaned on a regular basis.

The coils and fins of air systems are presently cleaned with acid, alkaline or neutral cleaners. Hand pump garden sprayers and hoses are the most commonly used form of a cleaner applicator. Acid and alkaline cleaners can be corrosive to the coils and fins and can over time cause serious damage. In any event, these types of cleaners are typically used on heavily fouled air systems. Often, metal fin rakes and brushes are also used to help clean off heavy buildup. However, this can cause additional damage to the air system.

An alternative to hand pump garden sprayers and the like are high pressure cleaning applicators (e.g., over 600 PSI). At these higher pressures, the coils, fins and the like of the air systems can become damaged as well. Moreover, known coil cleaning processes can require a significant amount of clean-up after use and can be time consuming and/or labor intensive to set-up and operate. This is due, in part, to the large amount of water and solutions that are used at flow rates that typically exceed 1 gallon per minute. This can create a disincentive for regular cleaning, particularly since air systems are typically out of view of occupants, management and the like.

A need therefore exists to improve surface cleaning, such as to improve the cleaning of surfaces associated with air handler systems, particularly the coils and fins thereof.

SUMMARY OF THE INVENTION

The first aspect of the instant claimed invention is an apparatus for cleaning a surface comprising: a pump and an applicator connected to the pump through which one or more cleaning agents can be applied to the surface at an operating pressure that is about 600 PSI or less and an operating flow rate that is about 1 gal/min or less.

The second aspect of the instant claimed invention is a surface cleaning system comprising:

a pump that operates at an operating pressure of about 600 PSI or less;

an applicator connected to the pump through which a fluid can flow at an operating flow rate that is about 1 gal/min or less;

a water supply that can be applied to a surface through the applicator at the operating pressure and the operating flow rate; and a cleaning agent supply that can be applied to the surface through the applicator at the operating pressure and the operating flow rate.

The third aspect of the instant claimed invention is a cleaning process, the cleaning process comprising the steps of:

applying a chemical cleaning agent to a surface in need of cleaning at an operating pressure that is about 600 PSI or less; and rinsing the surface with water supplied at the operating pressure.

DETAILED DESCRIPTION OF THE PRESENTLY PREFERRED EMBODIMENTS

The present invention generally relates to apparatuses, systems and methods for cleaning surfaces, such as surfaces associated with air handler systems, particularly, the coils and fins associated with these systems wherein dust, smoke, lint and other airborne constituents can be deposited on the surface thereof during use of same, thus rendering these surfaces in need of cleaning.

The present invention can be effectively used to clean a number of different types of surfaces associated with a variety of types of products, equipment and the like including those used for industrial purpose, commercial purpose, residential purpose and/or the like. For example, the present invention can be effectively used to clean air handler systems, such as HVAC systems, particularly the coils and fins that can collect deposits of airborne constituents, such as dust, pollen, mold and/or the like, on surfaces thereof during use. If not properly cleaned, this can adversely impact the heat transfer efficiency of these systems. Further, this can increase the potential for transmitting airborne pathogens into the room or building that use the air system as an unclean air system can act as a breeding ground for same.

Applicants have discovered that cleaning agents, such as chemical cleaners, biocides, biostatics, and/or the like, can be applied under lower pressures and at lower flow rates as compared to typical cleaning processes while at the same time providing better cleaning even at faster cleaning rates, such as two to three times faster than typical cleaning process times. At the lower pressures and flow rates, less water and/or cleaning solutions can be used. In this regard, less mess is associated with the operation of the cleaning apparatuses, systems and methods of the present invention as compared to typical cleaning processes that can use high pressure systems and/or high flow rates. This makes the present invention well suited for in-room use applications, such as the cleaning of air systems in hotel rooms and/or the like. Thus, the coils, fins and other associated parts of air systems can be cleaned better, faster, and remain clean over longer periods of time. Further, labor, energy, water/product, and facility downtime can be greatly reduced. Importantly, in-door air quality can be improved, and air handler system life can be extended, while the transmission of odors, airborne pathogens and/or the like through the air systems can be greatly minimized, if not completely eliminated.

It should be appreciated that the present invention is not limited to its use and application to air system cleaning as discussed above. The present invention can be applied in a number of different and suitable applications including indoor and outside use. For example, the present invention can be used for dumpster maintenance, drain maintenance, duct cleaning and/or the like. As previously discussed, the present invention can be used to remove and clean surfaces of airborne constituents that have collected thereon, such as dust, dirt, pollen, mold and/or the like. In addition, the present invention can be applied to clean any variety of different constituents and matter that have been transmitted through air, water and/or other medium and then deposited on the surface to be cleaned.

As previously discussed, the present invention can provide effective cleaning with cleaning agent solutions at lower operating pressures and flow rates. In an embodiment, the operating pressures are about 600 pounds per square inch ("PSI") or less including any suitable pressure defined within this range, such as from about 60 PSI to about 600 PSI, preferably about 100 PSI to about 600 PSI. With respect to flow rate, the present invention, in an embodiment, includes an operating flow rate that is less than about 1 gallon per minute ("gal/min") including any suitable flow rate defined within this range, such as about 0.1 gal/min to about 1.0 gal/min, preferably about 0.25 gal/min to about 0.5 gal/min.

At these operating pressures and flow rates, any number and suitable types and amounts of cleaning agents can be applied to clean the surface and in any suitable manner. The cleaning agents can include, for example, chemical cleaning agents, biocides, biostatics, deodorizers, sanitizers and/or other suitable agents. The chemical cleaning agents can include any suitable type of chemical cleaner, such as surfactant-based cleaners that are commercially-available or suitably manufactured. The surfactants can include any suitable form, such as anionic, cationic, and other suitable forms, charged and/or neutral.

The chemical cleaner agents in solution form can be applied to the surface in need of cleaning at a variety of different pH levels depending on the cleaning application. The chemical cleaning solution are made by diluting a chemical cleaner concentrate with water or other aqueous medium at a specified dilution ratio as described below in greater detail. In an embodiment, the chemical cleaning solutions have a pH that ranges from about 2.0 to about 14.0, including any suitable pH defined within this range. The cleaning apparatuses and systems of the present invention can use alkaline chemical cleaning solutions, pH balanced chemical cleaning solutions, acidic chemical cleaning solutions and/or the like. In an embodiment, the alkaline chemical cleaning solutions have a pH that ranges from about 8.0 to about 12.5; the pH balanced chemical cleaning solutions have a pH that ranges from about 5.0 to about 10.0; and the acidic chemical cleaning solutions have a pH that ranges from about 2.0 to about 4.0. However, it should be appreciated that the surfactant-based cleaners can be applied at any suitable or suitable number of pH levels during cleaning depending on the application.

In addition to chemical cleaning agents and solutions thereof, the present invention can use biocides, biostatics, solutions thereof and the like. The biocides, biostatics and the like include cleaning agents that can inhibit growth of bacteria, mold and the like and can include commercially-available products, such as CoilClear™ available from Ondeo Nalco, or suitably manufactured products. The chemical cleaning agents, biocides and biostatics in addition to other additional cleaning agents (i.e., deodorizers, sanitizers and the like) can include any suitable type of product, for example, any suitable commercially-available product, or product manufactured in any suitable way. For example, the chemical cleaners can include a solvent, such as a water-based solvent, an oil-based solvent and/or the like, to facilitate the cleaning process. The amount and type of solvent and/or other additional other cleaning constituents are generally known in the art, such as the amount and type of solvent that are used with commercially-available chemical cleaning products.

Prior to application on the surface, the cleaning agents are formed into a solution, such as water-based solution as previously discussed. In this regard, the cleaning agent in concentrate form, such as liquid, powder or the like, is dispersed and mixed with water or other suitable aqueous liquid at a suitable dilution ratio to form the solution. In an embodiment, the dilution ratio ranges from about 1:4 to about 1:256.

The apparatuses and systems of the present invention can include any number and type of suitable components. Preferably, the present invention provides a mobile and self-contained apparatus and system that can be effectively used to apply the cleaning agents in solution form at effective operating pressures and flow rates as discussed above. In an embodiment, the present invention includes a self-contained mobile cart that is equipped with the various components of the present invention, such as the cleaning agents, water supply, dilution unit, applicator, pump, hoses, fittings and/or other suitable cleaning components. The mobile cart or other suitable device can be equipped with the various cleaning components in any suitable manner.

In use, the cleaning agents are formed into a solution, such as a water-based solution, prior to application to the surface in need of cleaning as previously discussed. Once prepared, the cleaning agent solutions are ready for use. In an embodiment, the cleaning process includes applying a chemical cleaning agent solution at operating pressures and flow rates as discussed above. Next, the surface is rinsed with a suitable amount of a rinse solution, such as water, at the operating pressures and flow rates.

Subsequent to the rinse process, the biocide and/or biostatic cleaning solution can be applied at the operating pressures and flow rates. The biocide and/or biostatic act to inhibit growth of bacteria, mold and/or the like as discussed above. In addition, the biocide/biostatic essentially acts to coat the surface so as to effectively extend the timeframe between cleanings. In this regard, the biocide/biostatic coat can make the surface less susceptible to deposition of airborne constituents and/or the like. It should be appreciated that the cleaning process can be carried out in any suitable manner and under any suitable conditions. Preferably, the process as described above is applied to cleaning coils, fins and other associated parts of air handler systems as previously discussed. But, the cleaning process of the present invention can be used and/or modified to be used for a variety of different and suitable applications.

By way of example and not limitation, examples of the present invention are provided below.

EXAMPLE ONE

In-Room Unit

Figure 1:
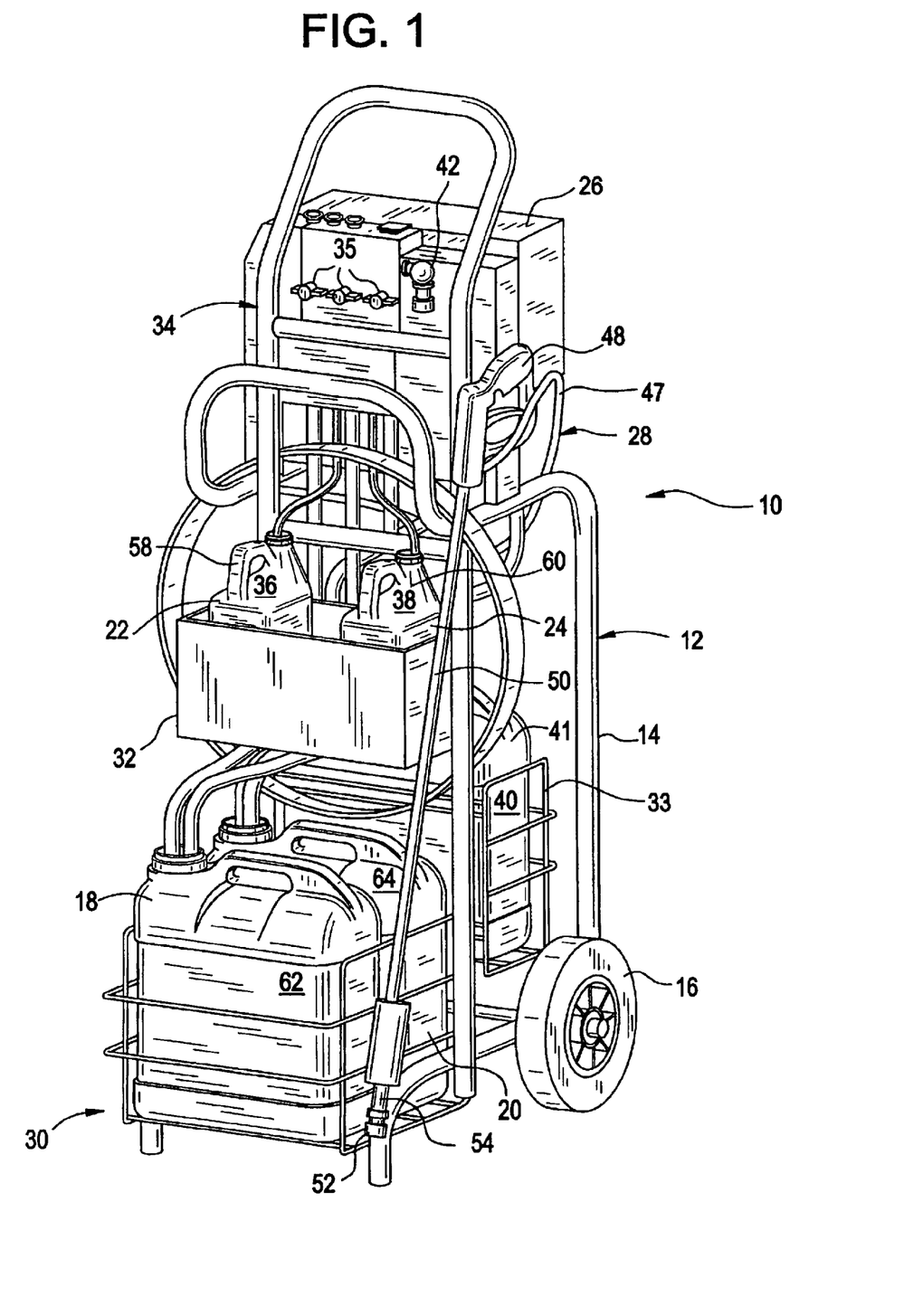
FIG. 1 is a perspective view of a cleaning apparatus and system in accordance with an embodiment of the present invention.
Figure 2:
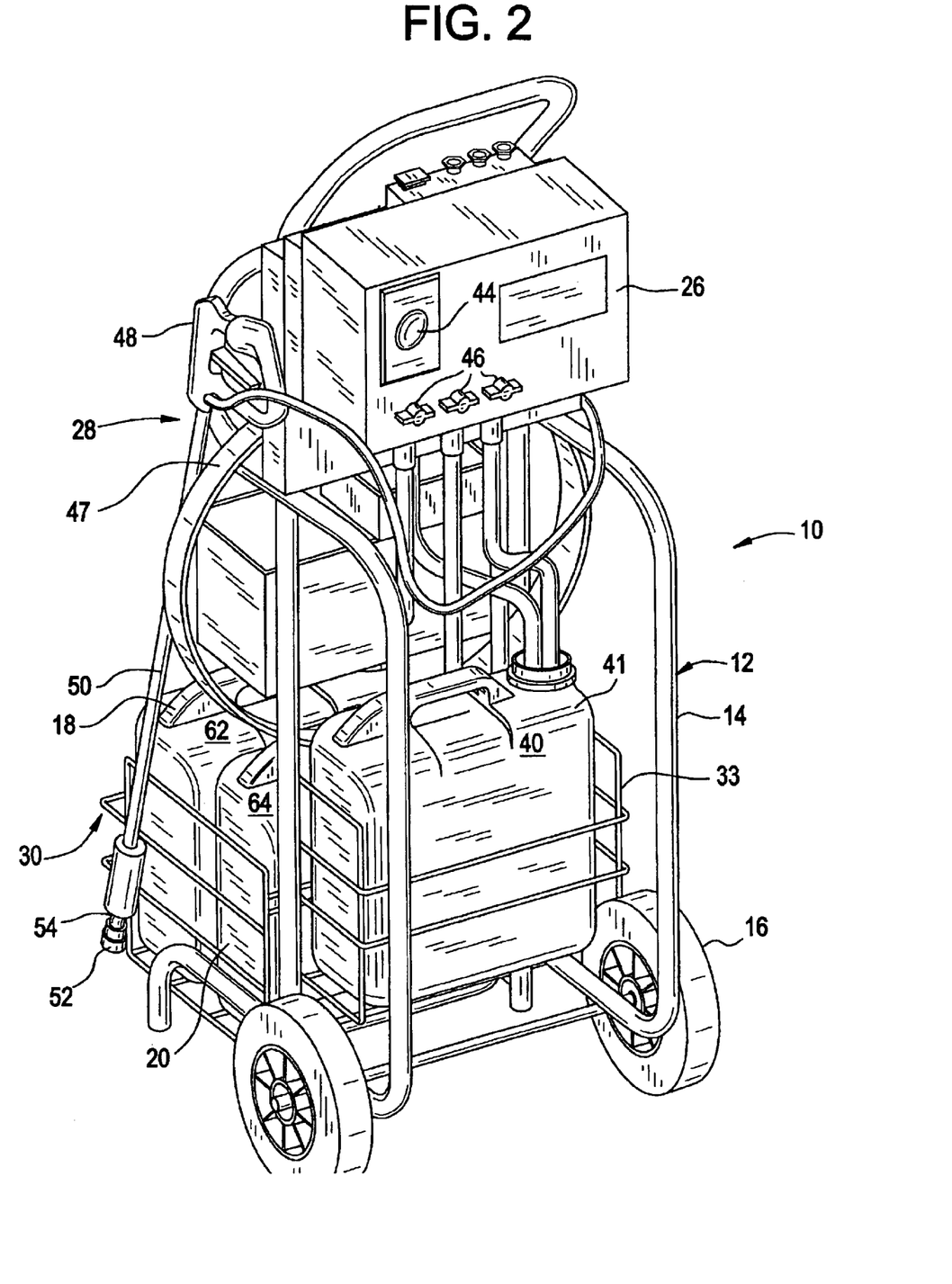
FIG. 2 is another perspective view of the cleaning apparatus and system as shown in FIG. 1.

In an embodiment, the present invention can provide effective cleaning that is well-suited for in-room use, such as in a hotel room, an office, a residence and/or the like. As shown in FIGS. 1 and 2, the cleaning apparatus and system 10 of the present invention includes a cart 12 that includes a frame 14 made from any suitable metal and alloys thereof and/or other suitable materials. The cart 12 also includes a pair of wheels 16 connected to the frame 14. This allows the cart 12 to be readily moved from one cleaning job to the next and during use of same.

As previously discussed, the mobile cart 12 is equipped with the cleaning components, thus providing a self-contained unit. As shown in FIGS. 1 and 2, the mobile cart 12 is equipped with a first cleaning agent solution container 18, a second cleaning agent solution container 20, a first cleaning agent concentrate container 22, a second cleaning agent concentrate container 24, a pump (not shown), a dilution unit (not shown), a housing for the pump and dilution system 26, and an applicator 28. The pump can be any suitable commercially available pump such as an electrically powered pump or battery powered pump The first and second cleaning agent solution containers 18, 20 are held within a device connected to the cart such as a basket 30 as shown in FIGS. 1 and 2. The basket 30 can be constructed in any suitable way, such as a wire basket construction as shown in FIGS. 1 and 2. The first and second cleaning agent concentrate containers 22, 24 are positioned in a holding device attached to the cart as shown in FIGS. 1 and 2. The holding device can be constructed in any suitable design, such as rectangular box configuration 32 as shown in FIGS. 1 and 2 and made from any suitable material, such as metal, alloys and the like. Another holding device is attached to the cart opposite and positioned above the basket 30. As shown in FIGS. 1 and 2, the holding device includes a wire basket configuration 33 that can be made from any suitable materials. The holding device 33 is used to support a container that contains rinse water as discussed below.

The housing 26 is attached to a top portion 34 of the mobile cart 12 but can be attached at any suitable location. The housing 26 encloses the pump and the dilution system.

The housing 26 includes a number of valves 35 associated with the dilution system. The valves 35 are in fluid communication with the first cleaning agent concentrate 36, the second cleaning agent concentrate 38 and the rinse water 40 stored within rinse water container 41. The valves 35 are used to regulate the flow of desired product or rinsing water as shown in FIG. 1. Any suitable commercially-available valves can be used for valves 35.

The in-line water connector 42 can be connected via a hose or the like (not shown) to a water supply (not shown), such as from a sink faucet, an outdoor water faucet or the like. In this regard, the water from the water supply is used to prepare the cleaning agent solutions and also to fill the rinse container 41 with rinse water 40 prior to use.

In general, the hydraulic force of water moving through the transfer tubes (not shown completely) from the water supply into the first and second cleaning agent solution containers 18 and 20, creates a vacuum to draw out the respective cleaning agent concentrate to dispense and mix with water from the water supply, thus forming the cleaning agent solution that is stored in each respective cleaning agent solution container. In an embodiment, the cleaning agent concentrates are drawn out of their respective cleaning agent concentrate containers to mix with the water from the water supply at a flow rate of about 5 gal/min.

As shown in FIG. 2, the housing 26 includes an on/of switch 44 for operating the pump, dilution units and/or other component parts. The cleaning apparatus and system 10 of the present invention can be powered by a battery or other portable power source and/or can be powered by an external power source. As shown in FIG. 2, the housing provides three separate valves 46 that control the flow of the chemical cleaning agent solution, the biocide/biostatic solution and the rinse water via the pump during use.

The applicator 28 is attached to the pump within the housing 26 via a hose 47. As shown in FIGS. 1 and 2, the applicator 28 is in the form of a spray gun that includes a handle 48 connected to a cylindrical part 50 with a nozzle 52 connected at an end 54 thereof to regulate the flow of cleaning solution as it is applied to the surface. The cylindrical part can be made of any suitable material and formed into a rigid, semi-rigid or flexible part.

In an embodiment, the pump flow rate and spray nozzle 52 are adjusted to regulate the operating flow rate at about 1 gal/min or less, preferably about 0.5 gal/min or less, such as about 0.25 gal/min or less as applied for in-room use. During use, the pump is operated at a pressure of about 100 PSI or less. The concentrates within the cleaning agent concentrate containers, the solutions within cleaning agent solution containers and the water 40 within the rinse water container 41 are in fluid communication with the pump and dilution system enclosed within the housing 26 via a number of different hoses. At these operating pressures and flow rates, the present invention is ideal for in-door use, such as cleaning air handler systems within a hotel room or other enclosed space. In this regard, the present invention can provide effective cleaning of unclean surfaces, such as coils and fins, while using a minimal amount of cleaning solution and/or water such that the amount does not exceed or does not substantially exceed the water storage capacity of the air handler system, such as a drip pan, drain or the like that is typically provided with such in-door air handler units.

As shown in FIG. 1, the chemical cleaning agent concentrate 60 is stored in the first cleaning agent concentrate container 22, the biocide and/or biostatic concentrate 58 is stored in the second cleaning agent concentrate container 24, chemical solution 64 is stored in the first cleaning agent solution container 18, and the biocide and/or biostatic solution 62 is stored in the second cleaning agent solution container 20. The containers can be made of any suitable material and sized in any suitable shape and with capacity for any suitable volumetric amount. As shown in FIGS. 1 and 2, the concentrate containers, chemical cleaning solution container and the rinse water containers can be made of any suitable material and sized and shaped in any suitable way, preferably ranging in size from about 0.5 gallons to about 5 gallons including any suitable volumetric size defined within this range, such as about 2.5 gallons or less for the cleaning and rinse water solution containers. The concentrate containers are generally smaller in capacity than the cleaning solution containers, such as about 1 gallon or less.

EXAMPLE TWO

Detachable Unit

Figure 3:
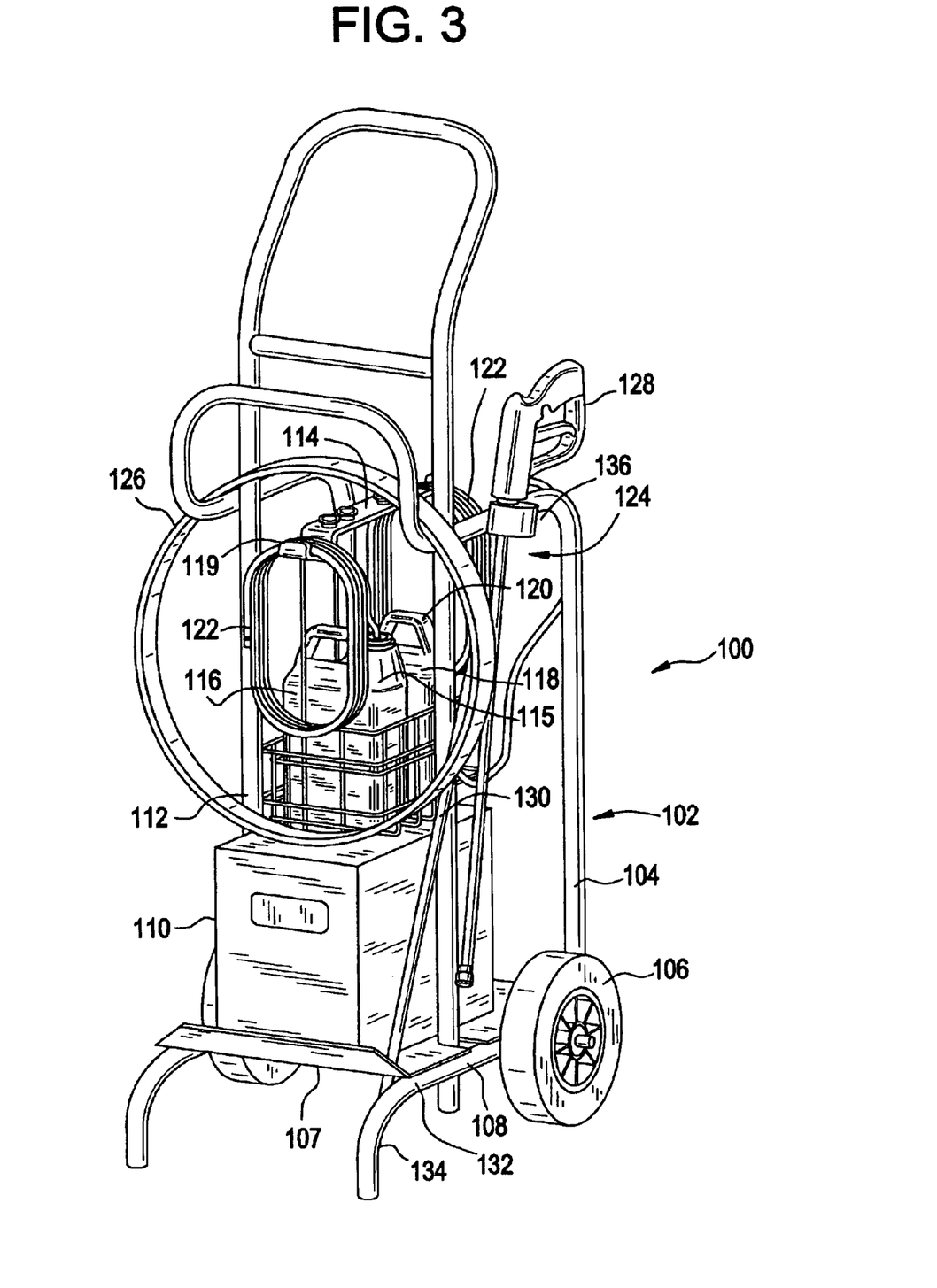
FIG. 3 is a perspective view of a cleaning apparatus and system in accordance with another embodiment of the present invention.
Figure 4:
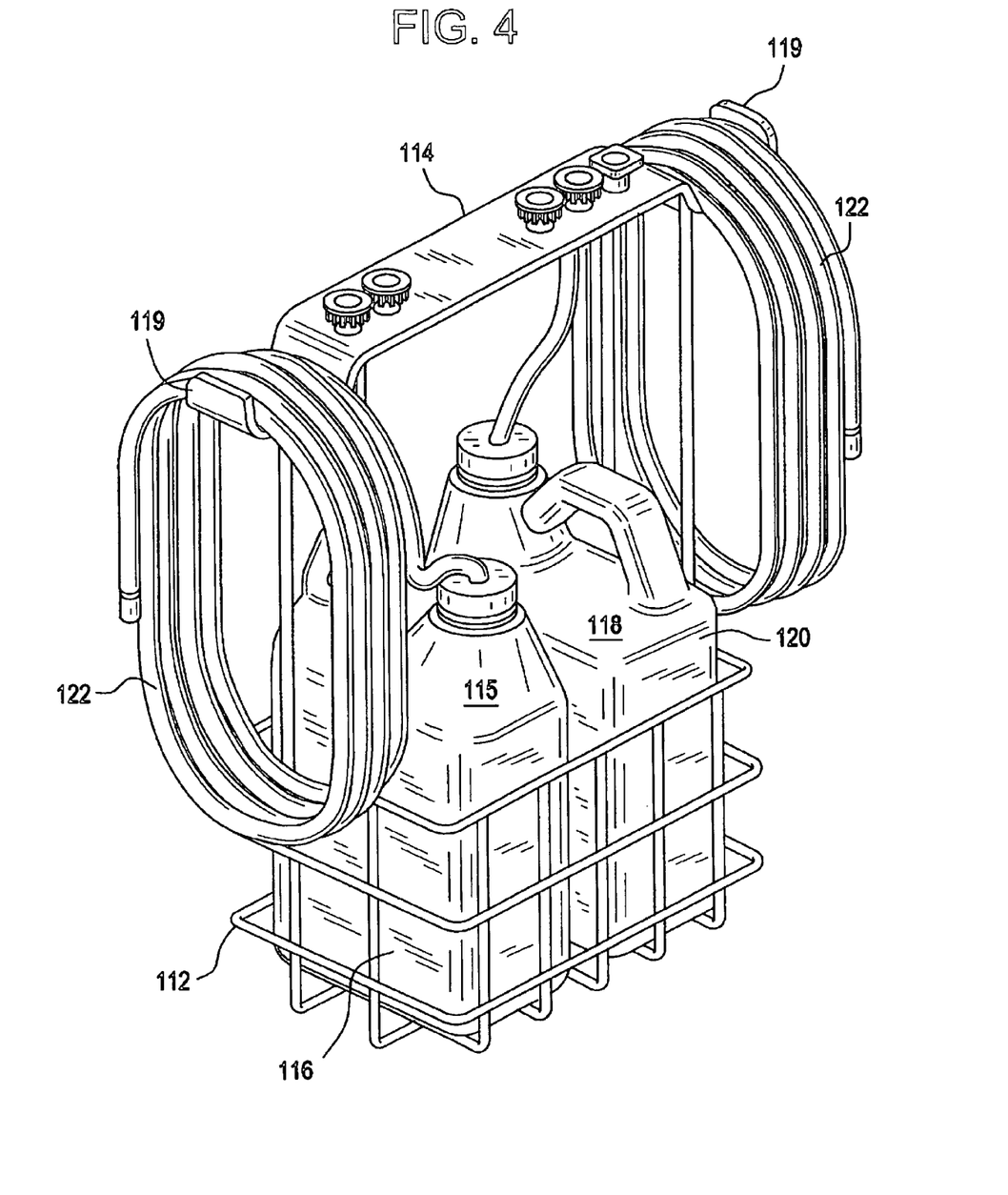
FIG. 4 is a perspective view of a detachable cleaning agent part of the cleaning apparatus and system of FIG. 3.

In an embodiment, the present invention provides a mobile cleaning apparatus and system 100 with one or more detachable cleaning components. As shown in FIGS. 3 and 4, the present invention provides a cleaning apparatus and system 100 that is well suited for outdoor use and indoor use, such as cleaning air handler systems that are located on roof tops or other outdoor and/or indoor locations that are not readily accessible or coils or larger/deeper coils that need to be cleaned with higher pressure. During this application, the operating pressures and flow rates are maintained at a relatively low level but are increased as compared to the operating pressures and flow rates discussed above in Example One, particularly for outdoor use. In an embodiment, the operating pressure ranges from about 100 PSI to about 600 PSI and the operating flow rate is about 0.5 gal/min or less.

Further, the detachable unit 100 provides a detachable construction that should facilitate use thereof, particularly if the cleaning operation is conducted on the roof or other elevated level. As shown in FIGS. 3 and 4, the present invention includes a mobile cart 102 that includes a frame 104 generally made from any suitable material including metal, alloys and the like. Two wheels 106 are attached to the frame 104 similar to the mobile cart 102 design in Example One.

The mobile cart 102 also includes a platform 107 attached to a bottom part 108 of the frame 104. The platform 106 can be made of any suitable material, such as wood, metal, plastic or the like, and attached to the frame 104 in any suitable manner. A housing 110 is located on the platform 106 wherein the housing 110 encloses the pump and other associated electronics (not shown) to power the cleaning apparatus and system 100 of the present invention.

The mobile cart 102 also includes a basket 112 with a handle 114 allowing the basket 112 to be detachably mounted to the frame 104. However, the basket 112 can be detachably mounted in any suitable manner. The basket 112 can be made of any suitable material, such as a metal wire material or the like with sufficient strength to support the weight of the cleaning agent concentrates as shown in FIGS. 3 and 4. The cleaning agent concentrates include a chemical concentrate 115 stored in a first container 116 and a biocide/biostatic 118 stored in a second container 120. In another embodiment there may be two of container 116 present for applications that require a larger amount of cleaning concentrate 115. The containers can include any suitable size and shape, such as ranging from about 16 ounces to about 5 gallons. The handle 114 further provides an arm portion 119 on both sides of the handle 114. The arm portion 119 is used to support hose 122 in fluid communication with the cleaning agent concentrates in the first and second containers.

An applicator 124 is also attached to the pump (not shown) via a hose 126 supported on the cart 102. The applicator 124 is similar in design as previously discussed in that the applicator includes a handle 128 connected to a cylindrical portion 130 that extends to an end 132 with a nozzle 134 to regulate flow therethrough. In addition, the applicator 124 is provided with a connector 136 attached at or near the handle 128. The connector 136 allows fluid connection between the applicator 124 and the cleaning agent concentrate during use. The connector can include any suitable type of connector, such as a quick connector that provides ready connection or the like.

In this regard, the pump is run at operating pressure or pressures to cause water flow through the applicator 124 at a regulated flow rate. The water is provided from an external water source (not shown), such as an outdoor water faucet connected to the pump through the housing 110. As the water flows through the applicator 124, the cleaning agent concentrate can be drawn out from the container and then dispensed and mixed with the water. The cleaning agent concentrate is connected to the applicator via the hose 122 when connected to the connector 136. This forms a cleaning agent solution for application to the surface to be cleaned. The dilution ratio of concentrate to water in the cleaning solution can be regulated with a metering tip or other suitable flow regulator device (not shown). The metering tip can be connected to a portion of the hose at any suitable position between the concentrate container and the applicator.

In use, the basket 112 can be detached from the cart and carried to an elevated area, such as a roof top, for cleaning purposes as shown in FIG. 4. This gives the user greater flexibility depending on the position and location of the equipment and surface thereof to be cleaned.

As previously discussed, the present invention can be used for cleaning purposes in a number of different applications, such as cleaning coils, fins and other like parts associated with an air handler system. It is believed that the present invention can provide enhanced cleaning in less time, such as at least one fifth to at least one half of the amount of time it takes to clean under typical conditions. This can be done using less water and cleaning solutions, thus minimizing the risk of water overflow and spills during use, particularly important during in-door use with respect to coil cleaning and the drain capacity associated with same. This can also reduce the "downtime" between cleaning jobs as less time may be necessary to clean-up after use. Set-up times can also be minimized as the present invention can be provided in a mobile and self-contained construction and thus ready-to-use. Also, a significant reduction in energy costs can be realized. Further, the operating pressures and flow rates can minimize or effectively eliminate the potential for damage to the surface to be cleaned, such as the coils and fins of an HVAC unit, thus extending the life of capital equipment.

The present invention displays enhanced cleaning capabilities all the while using less water and cleaning solution as compared to typical surface cleaning operations as discussed above. For example, the cleaning apparatuses, systems and processes as applied to air handler cleaning operations can reduce the risk of *legionella* and/or other airborne pathogens during use and greatly minimize, or effectively eliminate, biological matter build-up on the air system (i.e., HVAC system) and odors emitted therefrom during use.

As previously discussed, the cleaning apparatuses, systems and processes can include any variety of types and amounts of cleaning components, illustrative examples of which are detailed above and shown in FIGS. 1–4. However, it should be appreciated that the present invention is not limited to these examples, such as those illustrated in FIGS. 1–4. In this regard, the present invention can include any suitable modification and change from the construction, design and application of the present invention as discussed above.

Figure 5:
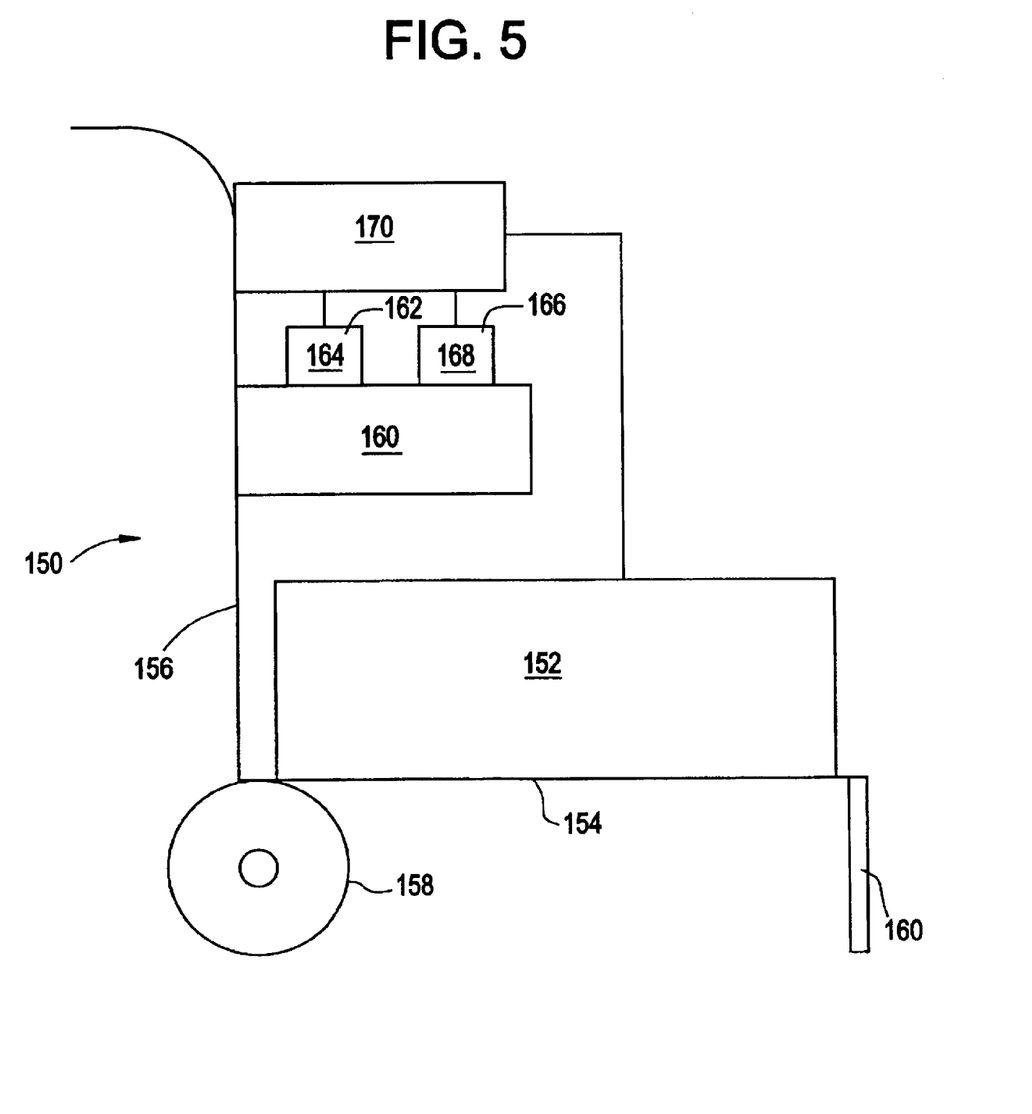
FIG. 5 is a perspective view of a cleaning apparatus and system in accordance with a further embodiment of the present invention.

For example, another illustration of the apparatuses and systems 150 of the present invention is shown in FIG. 5. This configuration as shown can be used as a substitute for in-room and/or outdoor configurations as discussed above and further illustrated in FIGS. 1–4. In this configuration, the systems and apparatuses 150 includes a water reservoir 152 that has a greater capacity than the rinse water containers as discussed above. In an embodiment, the water reservoir 152 includes a volume capacity that is about 6 gallons or less. The water reservoir 152 is positioned on a platform 154 attached to a lower portion of a mobile cart 156 as shown in FIG. 5. The mobile cart 156 can include any suitable design and be made from any suitable material as previously discussed. For example, the mobile cart 156 includes a pair of wheels 158 located at a back portion of the cart 156 and a support structure 160 for stationary purposes attached to a front part of the cart 158 as shown in FIG. 5. The support structure 160 can be replaced with one or more sets of wheels, if necessary, to provide greater mobility. In this regard, the cart 156 can include a brake mechanism attached to one or more of the wheels for stationary purposes.

A holding device 160 is attached to the cart at a location above the water reservoir but can be attached at any suitable location and in any suitable manner. The holding device 160 can be made of any suitable material as discussed above. As shown in FIG. 5, the holding device 160 acts to hold a first concentrate container 162 that contains a chemical cleaning agent concentrate 164 and a second concentrate container 166 that includes a biocide/biostatic concentrate 168. One or more additional concentrate containers can be used and attached to the cart in any suitable manner. Any variety and type of chemical cleaners, biocides, biostatics and/or the like can be used as discussed above.

A housing 170 is attached to the cart at a location positioned above the cleaning concentrates but can be mounted at any suitable location. The housing 170 encloses a pump (not shown) and further includes a number of valves, fittings and/or other connectors (not shown) necessary to establish fluid communication in the apparatuses and systems during use. The housing 170 can also contain the electronics, such as an on/off switch that can be powered with a portable battery and/or an external power source as previously discussed. In the alternative, the pump can be housed in a housing separate from the valve arrangement necessary to provide fluid communication in the system and apparatus of the present invention. The system and apparatus as shown in FIG. 5 can include a number of additional other components including an applicator (not shown) and the like as discussed above. The applicator is connected to the pump and is used to apply water and/or the cleaning solutions to the surface in need of cleaning as previously discussed.

In use, the water reservoir is filled with a necessary amount of water, such as to volume capacity. The cart can then be wheeled into the room or other area for cleaning purposes. The pump is operated at operating pressures, such as about 100 PSI or less as discussed above. The chemical cleaner is applied in solution form to the surface in need of cleaning. In this regard, the chemical cleaner solution is made by dispersing the chemical cleaning concentrate and mixing same with a water supply that flows from the water reservoir under pressure activated from the pump. The mixing can occur in any suitable manner depending on the valve arrangement of the systems and apparatuses of the present invention. The amount of chemical agent in solution can be regulated by a metering tip or other like device that is positioned at any suitable location, such as along the hose that fluidly connects that chemical agent to the pump. The solution can be mixed at any suitable dilution ratio as discussed above. Once mixed, the chemical solution is applied to the surface via the applicator that controls the flow therefrom at a suitable operating flow rate as further discussed above.

After the chemical cleaner solution has been applied, the valve arrangement is reconfigured to allow the surface to be rinsed with water from the water reservoir at the operating pressures and flow rates. After completion of the rinse cycle, the valve arrangement is again reconfigured in a suitable manner such that the biocide/biostatic agent can be applied in solution form to the surface. Depending on the cleaning application, the cleaning system and apparatus set-up as shown in FIG. 5 and suitable modifications thereof may be preferred as compared to the set-up as shown in FIGS. 1–4, particularly FIGS. 1 and 2 as applied to in room use. The set-up in FIG. 5 provides fewer containers to be carted from one job to the next (i.e., one room to the next). Further, it has a larger water capacity. This can facilitate the cleaning process, particularly where the amount of water supply is fixed and depends on the size of the container that carries same. Thus, down-times may be minimized due to the need to re-fill with water from a source that is outside of the room or area where the cleaning occurs, such as in a hotel room or other room enclosure.

The various other cleaning components of the present invention can be constructed in any suitable way depending on the application. For example, the nozzle can be configured in a number of suitable ways to provide better and easier access to the surface to be cleaned. In this regard, the nozzle or other suitable end portion of the applicator can be configured in a substantially straight path or a curved path of varying degrees, such as from 45° to 180°. The curved configuration can facilitate use of the present invention in less accessible places, It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. An apparatus for cleaning a surface, the apparatus comprising a pump, an applicator connected to the pump through which one or more cleaning agents can be applied to the surface at an operating pressure that is about 600 PSI or less and an operating flow rate that is about 1 gal/min or less, a basket which holds said cleaning agents, and a mobile cart that is equipped with the pump, the cleaning agents, the applicator, and the basket, wherein said basket is detachable from said mobile cart.

2. The apparatus of claim 1 wherein the cleaning agents are selected from the group consisting of a chemical cleaning agent, a biocide, a biostatic, solutions thereof and mixtures thereof.

3. The apparatus of claim 2 wherein the chemical cleaning agent includes a surfactant-based cleaning agent.

4. The apparatus of claim 2 wherein the chemical cleaning agent in solution form has a pH that ranges from about 2.0 to about 14.0.

5. The apparatus of claim 1 further comprising a dilution unit attached to the mobile cart wherein the dilution unit is capable of preparing the cleaning agents in solution form prior to application to the surface.

6. A surface cleaning system comprising:
- a pump operates at an operating pressure of about 600 PSI or less;
- an applicator connected to the pump through which a fluid can flow at an operating flow rate that is about 1 gal/min or less;
- a water supply that can be applied to a surface through the applicator at the operating pressure and the operating flow rate;
- a cleaning agent supply that can be applied to the surface through the applicator at the operating pressure and the operating flow rate;
- a basket which holds said cleaning agent supply;
- and a mobile cart that is equipped with the pump, the cleaning agents, the applicator, and the basket, wherein said basket is detachable from said mobile cars.

7. The surface cleaning system of claim 6 further comprising a mobile cart that is equipped with the pump, the applicator, the water supply and the cleaning agent supply.

8. The surface cleaning system of claim 7 wherein the cleaning agent supply is detachably connected to the mobile cart.

9. The surface cleaning system of claim 6 wherein the water supply includes a water reservoir.

10. The surface cleaning system of claim 6 wherein the water supply is supplied by an in-line water connector through which water is provided from an external water source.

11. The surface cleaning system of claim 6 wherein the cleaning agent supply is selected from the group consisting of a chemical cleaning agent, a biocide, a biostatic, solutions thereof and mixtures thereof.

12. The surface cleaning system of claim 11 wherein the chemical cleaning agent includes a surfactant-based cleaning agent.

13. The surface cleaning system of claim 12 wherein the chemical cleaning agent in solution form is selected from the group consisting of an alkaline solution having a pH m about 8.0 to about 12.5, a pH balanced solution having a pH from about 5.0 to about 10.0, an acidic solution having a pH ranging from about 2.0 to about 4.0, and mixtures thereof.

14. The surface cleaning system of claim 6 further comprising a dilution mechanism including a dilution unit capable of preparing the cleaning agent supply in solution form at a dilution ratio that ranges from about 1:4 to about 1:256.

* * * * *